US00PP36146P3

(12) United States Plant Patent
Schoone

(10) Patent No.: US PP36,146 P3
(45) Date of Patent: Sep. 24, 2024

(54) ***PHALAENOPSIS* PLANT NAMED 'Anagram'**

(50) Latin Name: *Phalaenopsis hybrida*
Varietal Denomination: Anagram

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/527,335

(22) Filed: Dec. 3, 2023

(65) Prior Publication Data

US 2024/0188464 P1 Jun. 6, 2024

Related U.S. Application Data

(60) Provisional application No. 63/430,035, filed on Dec. 4, 2022.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02; A01H 5/00; A01H 6/62
See application file for complete search history.

*Primary Examiner* — June Hwu
(74) *Attorney, Agent, or Firm* — C. Anne Whealy

(57) ABSTRACT

A new and distinct cultivar of *Phalaenopsis* plant named 'Anagram', characterized by its relatively compact and upright plant habit; moderately vigorous growth habit; strong flowering stems; strong leaves; freely flowering habit with typically three inflorescences developing per plant, each inflorescence with numerous flowers; dark purplish red-colored flowers with narrow light purple-colored marginal edges; flowers with white, yellow and dark purplish red-colored labella; and good postproduction longevity.

2 Drawing Sheets

Figure 1:
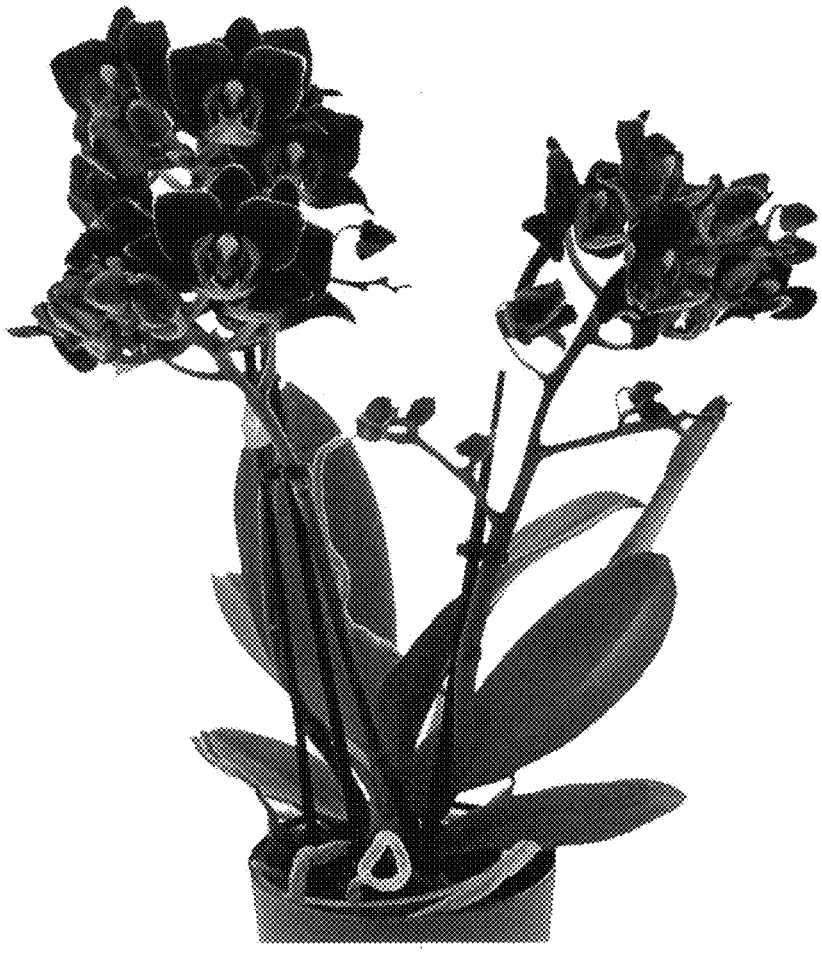

Botanical designation: *Phalaenopsis hybrida.*
Cultivar denomination: 'ANAGRAM'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Aug. 15, 2022, application number 2022/1907. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Anagram'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in February, 2014 in Assendelft, The Netherlands of a proprietary selection of *Phalaenopsis hybrida* identified as code number 18156, not patented, as the female, or seed, parent with a proprietary selection of *Phalaenopsis hybrida* identified as code number 5446, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in October, 2018.

Asexual reproduction of the new *Phalaenopsis* plant by in vitro meristem propagation in a controlled environment in Assendelft, The Netherlands since October, 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Anagram'. These characteristics in combination distinguish 'Anagram' as a new and distinct *Phalaenopsis* plant:

1. Relatively compact and upright plant habit.
2. Moderately vigorous growth habit.
3. Strong flowering stems.
4. Strong leaves.
5. Freely flowering habit with typically three inflorescences developing per plant, each inflorescence with numerous flowers.
6. Dark purplish red-colored flowers with narrow light purple-colored marginal edges.
7. Flowers with white, yellow and dark purplish red-colored labella.
8. Good postproduction longevity.

Plants of the new *Phalaenopsis* can be compared to plants of the female parent selection. Plants of the new *Phalaenopsis* differ primarily from plants of the female parent selection in the following characteristics:

1. Flower petals of plants of the new *Phalaenopsis* do not have any stripes whereas flower petals of the female parent selection have numerous stripes.
2. Lateral flower lobes of the plants of the new *Phalaenopsis* have a moderate amount of spots whereas lateral flower lobes of plants of the female parent selection do not have any spots.

Plants of the new *Phalaenopsis* can be compared to plants of the male parent selection. Plants of the new *Phalaenopsis* differ primarily from plants of the male parent selection in the following characteristics:

1. Flower petals of plants of the new *Phalaenopsis* have narrow light purple-colored marginal edges whereas flower petals of plants of the male parent selection have broader light purple-colored marginal edges.
2. Lateral flower lobes of the plants of the new *Phalaenopsis* have a moderate amount of spots whereas lateral flower lobes of plants of the male parent selection only have a few spots.

Plants of the new *Phalaenopsis* can be compared to plants of *Phalaenopsis hybrida* 'Cherry Valentine', not patented. In side-by-side comparisons, plants of the new *Phalaenopsis* differ primarily from plants of 'Cherry Valentine' in the following characteristics:

1. Central lobes of the labellum of plants of the new *Phalaenopis* are more rounded than cental lobes of the labellum of plants of 'Cherry Valentine'.
2. Lateral flower lobes of the plants of the new *Phalaenopsis* have a moderate amount of spots whereas lateral flower lobes of plants of 'Cherry Valentine' only have a few spots.
3. Upper surface of pedicels of plants of the new *Phalaenopsis* are strongly tinged with anthocyanin whereas upper surface of pedicels of plants of 'Cherry Valentine' are slightly to moderated tinged with anthocyanin.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Anagram' grown in a container.

Figure 2:
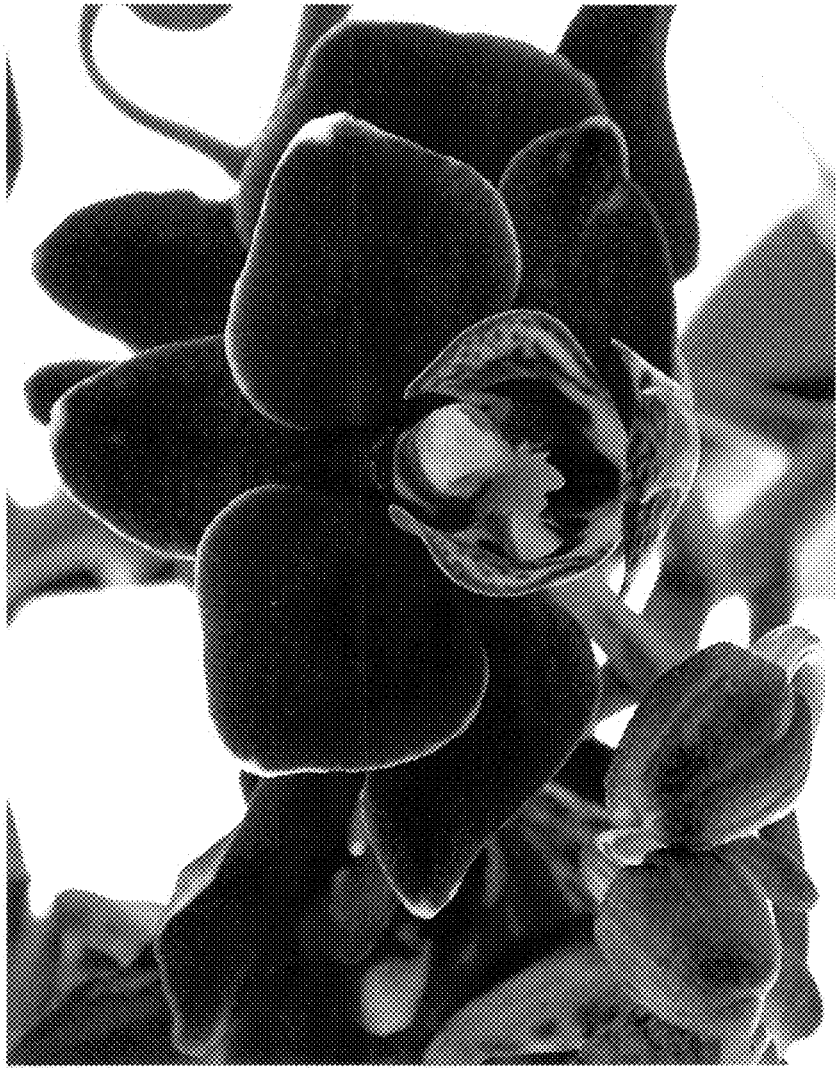

The photograph on the second sheet (FIG. 2) is a close-up view of typical flower buds and a typical flower of 'Anagram'.

DETAILED BOTANICAL DESCRIPTION

The aforementioned photographs and following observations and measurements describe plants grown during the summer in 9-cm containers in a glass-covered greenhouse in Heemskerk, The Netherlands and under cultural practices typically used in commercial *Phalaenopsis* production. Plants were 16 months old when the photographs and description were taken. During the first twelve months of production of the plants, day and night temperatures averaged 27 C. During the final four months of production of the plants, day temperatures ranged from 20 C. to 22 C. and night temperatures ranged from 18 C. to 20 C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Anagram'.

Parentage:

*Female, or seed, parent*.—Proprietary selection of *Phalaenopsis hybrida* identified as code number 18156, not patented.

*Male, or pollen, parent*.—Proprietary selection of *Phalaenopsis hybrida* identified as code number 5446, not patented.

Propagation:

*Type*.—By in vitro meristem propagation.

*Time to initiate roots, summer and winter*.—About two weeks at temperatures about 28 C. to 30 C.

*Time to produce a rooted young plant, summer and winter*.—About 20 to 25 weeks at temperatures about 28 C. to 30 C.

*Root description*.—Thin, fibrous; typically light yellowish white in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically three inflorescences developing per plant, each inflorescence with numerous flowers; monopodial; moderately vigorous growth habit and moderate to slow growth rate.

*Plant height, substrate level to top of foliar plane*.—About 15.1 cm.

*Plant height, substrate level to top of floral plane*.—About 27 cm.

*Plant diameter or spread*.—About 24.1 cm.

Leaf description:

*Arrangement and quantity*.—Distichous, simple; sessile; about four leaves per plant.

*Length*.—About 15.8 cm.

*Width*.—About 5.5 cm.

*Aspect*.—Outwardly arching.

*Shape*.—Narrowly oblanceolate; slightly carinate, and flat to slightly curled downward or upward.

*Apex*.—Unequal acute.

*Base*.—Sheathing. Sheath length: About 1.8 cm. Sheath width: About 1.2 cm. Sheath color: Close to 143C; marginal edges, close to 143B.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to a blend of NN137A and 147A. Developing leaves, lower surface: Close to 146A; marginal edges, tinged with close to NN137C. Fully expanded leaves, upper surface: Close to NN137B; venation, close to NN137A. Fully expanded leaves, lower surface: Close to 146B; venation, close to 143A.

Inflorescence description:

*Appearance and flowering habit*.—Showy zygomorphic flowers arranged on axillary simple or branched racemes; typically three inflorescences develop per plant; each inflorescence with about 14 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about five months after planting; plants flower naturally during the winter into the spring.

*Flower longevity*.—Long flowering period, individual flowers maintain good substance for about eight weeks on the plant; flowers not persistent.

*Inflorescence length* (*lowermost flower to inflorescence apex*).—About 12.1 cm.

*Inflorescence width*.—About 11.1 cm.

*Flower buds*.—Height: About 1.3 cm. Diameter: About 1 cm by 1.2 cm. Shape: Broadly ovate. Color: Close to a blend of N186B and N186C; proximal blotch, close to 148B and 148C.

*Flower size*.—About 3.8 cm (vertical) by 4.7 cm (horizontal).

*Flower depth*.—About 2.4 cm.

*Petals, quantity and arrangement*.—Three, two lateral petals and one center petal transformed into a labellum.

*Lateral petals*.—Length: About 2 cm. Width: About 2.2 cm. Shape: Roughly deltoid to lunate. Apex: Broadly and bluntly acute to narrowly obtuse. Margin: Entire; not undulate. Texture and luster, upper and lower surfaces: Smooth, glabrous, velvety; matte. Color: When opening, upper surface: Close to N186C; towards the margins, apex and base, close to 187B; narrow marginal edges, close to 76D. When opening, lower surface: Close to a blend of N186D and 187A; central irregular blotch, close to 76B; narrow marginal edges, close to 76D. Fully opened, upper surface: Close to N186D; central blotch, close to N186C; narrow marginal edges, close to 77D; color does not change with subsequent development. Fully opened, lower surface: Close to 187B; towards the margins and apex, close to N79B; central irregular blotch, close to 76A and 76B; narrow marginal edges, close to 76C; color does not change with subsequent development.

*Labella*.—Appearance: Three-parted with two lateral lobes and a central lobe. Length, lateral lobes: About 1.7 cm. Width, lateral lobes: About 1 cm. Length, central lobe: About 1.8 cm. Width, central lobe: About 5 mm to 15 mm. Length, cirrhose tips: About 2 mm. Shape, lateral lobes: Obovate. Shape, central lobe: Deltoid with a slightly elongated apex. Apex, lateral lobes: Obtuse. Apex, central lobe: Cleft with two upwardly curved cirrhose apices. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 3 mm in length, about 4 mm in width and about 4 mm in height. Color: When opening, upper surface: Lateral lobes: Close to 76B; towards the base, close to N186C; towards the margins, close to N78A and lower margins, tinged with close to 22D; blotch and spots, close to N78A and N79B. Central lobe: Close to 76A and 76B; central blotch, close to 11B; towards the margins, close to N186D; at the apex and cirrhose tips, close to N78A; at the base, close to a blend of N186C and 200A and towards the column, close to NN155D; blotches, close to N78A. Callosities: Close to N186C; apices, close to 17A. When opening, lower surface: Lateral lobes: Close to 76B; towards the margins, close to N78A and lower margins, tinged with close to 22D; at the base, close to N187C; blotch and spots, close to N79D. Central lobe: Close to 76B; central blotch, close to N78A; towards the margins, close to 71A; at the apex and cirrhose tips, close to N78B; at the base, close to N77D and towards the column, close to NN155D. Fully opened, upper surface: Lateral lobes: Close to 76B; towards the base, close to N186C; towards the margins, close to N78A and lower margins, tinged with close to 12B; blotch and spots, close to N78A and N79B. Central lobe: Close to 76A and 76B; central blotch, close to 11B; towards the margins, close to N186D; at the apex and cirrhose tips, close to N78A; at the base, close to a blend of N186C and 200A and towards the column, close to NN155D; blotches, close to N78A. Callosities: Close to N186C; apices, close to 17A. Fully opened, lower surface: Lateral lobes: Close to 76B; towards the margins, close to N78A and lower margins, tinged with close to 22D; at the base, close to N187C; blotch and spots, close to N78B. Central lobe: Close to 76B; central blotch, close to N78A; towards the margins, close to 71A; at the apex and cirrhose tips, close to N78B; at the base, close to N77D and towards the column, close to NN155D.

*Sepals*.—Quantity and arrangement: Three, one upper dorsal sepal and two lower lateral sepals. Length, dorsal sepal: About 2.4 cm. Width, dorsal sepal: About 1.4 cm. Length, lateral sepals: About 2.4 cm. Width, lateral sepals: About 1.6 cm. Shape, dorsal sepal: Narrowly ovate. Shape, lateral sepals: Ovate. Apex, dorsal sepal: Narrowly obtuse. Apex, lateral sepals: Bluntly acute. Base, dorsal and lateral sepals: Truncate. Margins, dorsal sepal: Entire; not undulate. Margins, lateral sepals: Entire; coarsely undulate. Texture and luster, dorsal and lateral sepals, upper surface: Smooth, glabrous, moderately velvety; matte. Texture and luster, dorsal and lateral sepals, lower surface: Smooth, glabrous, slightly velvety; matte. Color, dorsal sepal: When opening, upper surface: Close to N186C; towards the margins, apex and base, close to 187B; apices, close to 76B. When opening, lower surface: Close to N186D; central blotch, close to 186D; apices, close to 76B. Fully opened, upper surface: Close to N186C; towards the margins, apex and base, close to N186D; apices, close to 76B; color does not change with subsequent development. Fully opened, lower surface: Close to a blend of N79B and 187A; central blotch and venation, close to 77A; apices, close to N78C; color does not change with subsequent development. Color, lateral sepals: When opening, upper surface: Close to N186C; towards the margins, apex and base, close to 187B; apices, close to 76B. When opening, lower surface: Close to N187A; center, strongly blushed with close to 198A; apices, close to N78B. Fully opened, upper surface: Close to N186C; towards the margins, apex and base, close to N186D; apices, close to 76B; color does not change with subsequent development. Fully opened, lower surface: Close to a blend of N79B and 187B; central blotch and venation, close to 76A; apices, close to N78A to N78B; color does not change with subsequent development.

*Peduncles*.—Length: About 24.9 cm. Diameter: About 5 mm. Strength: Strong. Aspect: Upright to outwardly arching. Texture and luster: Smooth, glabrous; matte. Color: Close to 147A; fine dots, close to 143B.

*Pedicels*.—Length: About 3 cm. Diameter: About 2 mm. Strength: Moderately strong. Aspect: About 70 degrees from peduncle axis. Texture and luster: Smooth, glabrous; matte. Color: Close to a blend of 144B and 146D; distally, close to 155C; upper surface, strongly tinged with close to 187B.

*Reproductive organs*.—Androecium: Column length: About 9 mm. Column width: About 6 mm. Column color: Close to N79C; towards the apex and base, close to 76C; at the base, close to N78D. Pollinia quantity: Two. Pollinia diameter (per two pollinia): About 2.5 mm. Pollinia color: Close to 23A. Gynoecium: Stigma length: About 4 mm. Stigma width: About 4 mm. Stigma shape: Reniform. Stigma color: Close to 76D; edges, close to N79C. Ovary length: About 1 cm. Ovary diameter: About 1 mm. Ovary color: Close to 150C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40 C. and are suitable for USDA Hardiness Zones 10 to 12.

It is claimed:

1. A new and distinct *Phalaenopsis* plant named 'Anagram' as illustrated and described.

* * * * *